(12) United States Patent
Reisinger et al.

(10) Patent No.: US 6,734,325 B2
(45) Date of Patent: May 11, 2004

(54) PROCESS FOR THE SEPARATION OF REACTION MIXTURES AND THE RECIRCULATION OF QUATERNARY SALTS

(75) Inventors: Claus-Peter Reisinger, Wixom, MI (US); Sven Michael Hansen, Leverkusen (DE); Peter Fischer, Köln (DE); Michael Traving, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/320,009

(22) Filed: Dec. 16, 2002

(65) Prior Publication Data

US 2003/0166959 A1 Sep. 4, 2003

(30) Foreign Application Priority Data

Dec. 27, 2001 (DE) .......................................... 101 64 145

(51) Int. Cl.$^7$ .............................. C07F 5/04; C07F 9/02; C07C 277/06

(52) U.S. Cl. ..................... 564/296; 564/230; 564/281; 558/146; 558/286; 568/9

(58) Field of Search ................................ 564/230, 281, 564/296; 568/9

(56) References Cited

U.S. PATENT DOCUMENTS

| | | | | | |
|---|---|---|---|---|---|
| 3,227,748 A | * | 1/1966 | Bragdon et al. | ............. | 260/501 |
| 3,484,348 A | * | 12/1969 | Johnson et al. | ................ | 204/73 |
| 4,172,782 A | * | 10/1979 | Masuko et al. | ........ | 260/567.6 H |
| 4,487,698 A | * | 12/1984 | Idel et al. | .................... | 210/639 |

FOREIGN PATENT DOCUMENTS

| EP | 0 763 521 A2 | * | 3/1997 | ......... | C07C/211/62 |
|---|---|---|---|---|---|
| EP | 0 913 197 | | 5/1999 | | |

\* cited by examiner

Primary Examiner—Brian Davis
(74) Attorney, Agent, or Firm—Joseph C. Gil; Gary F. Matz; Aron Preis (57) ABSTRACT

A process for the separation and recycling of catalyst components from a chemical reaction mixture is disclosed. The process entails at least one extraction step.

10 Claims, 4 Drawing Sheets

PROCESS FOR THE SEPARATION OF REACTION MIXTURES AND THE RECIRCULATION OF QUATERNARY SALTS

FIELD OF THE INVENTION

The present invention relates to a process and more particularly to the separation and the recycling of catalyst components from a chemical reaction mixture.

SUMMARY OF THE INVENTION

A process for the separation and recycling of catalyst components from a chemical reaction mixture is disclosed. The process entails at least one extraction step.

BACKGROUND OF THE INVENTION

Quaternary salts, for example tetraalkylammonium or tetraalkylphosphonium salts, are utilized in many reactions as a phase transfer catalyst, as a conducting electrolyte or in other functions. Because these compounds are costly it is important for the economics of industrial production processes that the quaternary salts are recovered from the reaction mixtures so that they can be re-utilized.

It is known (EP A1 913 197, U.S. Pat. No. 6,310,232, Handbook of Phase Transfer Catalysis, Y. Sasson, R. Neumann, editors, Blackie Academic, London 1997, p. 127 et seq.) that quaternary salts can be extracted from organic phases by means of water.

An example of the use of quaternary salts is diaryl carbonate production by oxidative direct carbonylation of aromatic hydroxy compounds in the presence of CO, 02 and a precious metal catalyst (see, for example, DE-A 27 38 437, U.S. Pat. No. 4,349,485, U.S. Pat. No. 5,231,210, EP-A 0 667 336, EP-A 0 858 991, U.S. Pat. No. 5,760,272). Palladium is preferably utilized as the precious metal. A co-catalyst (for example manganese salts or cobalt salts), a base, a quaternary salt, various quinones or hydroquinones and drying agents can additionally be dispensed-in. It is possible here to work in a solvent.

After the reaction has been carried out, product mixtures which comprise, inter alia, a hydroxyaromatic compound B, one or more quaternary salts A, reaction products C such as, for example, water and diaryl carbonates, as well as possibly solvent, further catalyst components, auxiliary substances and impurities, are obtained in these reactions. The object here is to separate one or more products C from the quaternary salts A and to return A into the reaction, as far as possible without impurities which are comprised in the reaction mixture.

DETAILED DESCRIPTION OF THE INVENTION

It has now surprisingly been found that this object may be achieved by various extractions whereof the course is controlled by way of the concentration of B.

The invention therefore provides a process I for the removal and recovery of quaternary salts A corresponding to the formula $(Q^{n+})_m(Y_{m-})_n$ from reaction mixtures which in addition to A also comprise one or more hydroxyaromatic compounds B and one or more reaction products C and as an option a solvent, the process comprising at least one of steps a) to e):

a)
    a1) adjusting the mass fractions $C_A$ of A and $C_B$ of B in the reaction mixture such that $0.001 \cdot c_A < c_B < 4 \cdot c_A$, preferably approximately $0.01 \cdot c_A < c_B < 3 \cdot c_A$, particularly preferably approximately $0.1 \cdot c_A < c_B < 1.5 \cdot c_A$, and     a2) extracting the reaction mixture with water or with an aqueous solution to obtain an aqueous phase that contains A and an organic phase which comprises C and optionally isolating C from the organic phase, b)
    b1) extracting an aqueous phase that contains A with an organic phase that contains 2 to 100 wt. % relative to the weight of the organic phase of B, and     b2) returning the organic phase into the reaction mixture optionally after isolating the quaternary salts A from the organic phase, c)
    c1) using the aqueous phase following the extraction referred to in b1) in the extraction referred to in a2), to form a closed water loop, d)
    d1) extracting the water phase resulting from the extraction referred to in b1) with an organic phase before the extraction a2) to obtain a water phase having reduced content of B and an organic phase, e)
    e1) adding B to the organic phase obtained in step d1), and using the result in step b1).

The process according to the invention may also entail any combination of at least two of the steps a) to e) according to the invention. Each of these combinations is provided by the present invention.

The separation process according to the invention may be carried out at temperatures of from −10 to 120° C. It has surprisingly been found when investigating the temperature-dependency of the reaction that in particular the step a2) may be carried out with increasingly marked improvement and having fewer stages at temperatures higher than room temperature, above all at concentrations of A>0.5 wt. %. On the other hand, it has been established that owing to the thermal stability of many quaternary salts A, it is obvious to carry out the process at temperatures below 100° C.

Temperatures of in each case from approximately 28 to 98° C. are therefore preferred, particularly preferably approximately 45 to 95° C., most particularly preferably approximately 70 to 93° C., for carrying out the steps a) to e). The pressure is in each case from approximately 0.1 to 200 bar, preferably 0.5 to 50 bar, particularly preferably 1 to 10 bar. Before the extraction steps a2), b1) and d1) are carried out, the aqueous phases preferably have a pH of from 1 to 10, particularly preferably a pH of from 2 to 8. The volumetric ratios of organic to aqueous phase lie in each case between approximately 0.01 to 100, preferably approximately 0.05 to 20, particularly preferably 0.1 to 10.

Substances having only limited miscibility with water, preferably being virtually immiscible and being chemically inert to the reagents A, B and C which are utilized, are utilized as the inert organic solvent. The solvent or solvent mixture preferably has a boiling point of from approximately 30 to 200° C., particularly preferably approximately 75 to 160° C.

Solvents having dielectric constants of less than approximately 20 are preferred, particularly preferably solvents having dielectric constants<15. The inert solvent may be included in the reaction mixture in a proportion of from 1 to 99 wt. %, preferably 20 to 98 wt. %, particularly preferably 40 to 98 wt. %. It may as an option be removed in whole or in part by distillation before the extraction is carried out, optionally an entrainment action may in this case be exploited in order to effect partial separation of B.

Hydrocarbons, halogenated hydrocarbons and aromatic solvents such as chlorobenzene, dichlorobenzene, fluorobenzene, benzene, toluene, the xylenes, anisole, methylene chloride, chloroform, cyclohexane or 1,2-dichloroethane, ethers such as dioxane, tetrahydrofuran, tert.-butylmethyl ether and etherified glycols, optionally also mixtures of various solvents, may, for example, be used as the solvent. Chlorobenzene is particularly preferably utilized.

Different solvents may in each case be utilized for the individual steps a2), b1) and d1). However, the use of the same solvent or solvent mixture for all the steps is preferred.

Even if the reaction has been carried out in solvent, the solvent utilized for that is generally preferably used.

For one or more part steps of the process it may optionally also be favourable to utilise a product C or the hydroxyaromatic compound B in excess as the solvent or as a component of a solvent mixture.

The aromatic hydroxy compounds B which are suitable according to the invention include compounds corresponding to the formula R-(OH)$_p$, in which R represents an aromatic radical. They are selected from the group comprising monohydroxylated aromatic compounds (p=1), dihydroxylated aromatic compounds (p=2) or polyhydroxylated aromatic compounds (2<p<=4) or bisphenols (p=2), which may have from 0 to 4 substituents such as $C_1$–$C_{18}$-alkyl or-cycloalkyl, $C_6$–$C_{18}$-aryl, $C_7$–$C_{18}$-aralkyl, $C_1$–$C_{18}$-alkoxy, fluorine, chlorine or bromine. The alkyl, aryl and aralkyl substituents may themselves be substituted or may carry functional groups such as ether groups, thioether groups, keto groups, epoxy groups, halogens, heterocyclic rings. Aromatic substituent rings may be annelated or bridged, a plurality of radicals may be bonded to form cycles.

Examples are monohydroxy compounds such as phenol; o-, m- or p-cresol; o-, m- or p-chlorophenol; alkyl phenols such as, for example, o-, m- or p-ethylphenol, o-, m- or p-propylphenol, o-, m- or p-tert.-butylphenol, o-, m- or p-isooctylphenol, o-, m- or p-stearylphenol; o-, m- or p-phenylphenol; o-, m- or p-cyclohexylphenol; o-, m- or p-methoxyphenol; 2,6-dimethylphenol, 2,4-dimethylphenol, 3,4-dimethylphenol; 1-naphthol, 2-naphthol or di- or polyhydroxy compounds such as resorcinol and hydroquinone, as well as bisphenols such as 2,2-bis(4-hydroxyphenyl) propane (bisphenol A), 2,2-bis(3,5-dimethyl-4-hydroxyphenyl)propane, 1,1-bis(4-hydroxyphenyl) cyclohexane, 1,1-bis(4-hydroxyphenyl)-3,3,5-trimethylcyclohexane (bisphenol TMC), α,α-bis(4-hydroxyphenyl)-m-diisopropylbenzene, 6,6'-dihydroxy-3,3, 3',3'-tetramethyl-1,1'-spiro-(bis)indane, 4,4'-dihydroxybiphenyl or 2,4'-dihydroxybiphenyl.

Mixtures of various aromatic hydroxy compounds may also be utilized, however a single hydroxy compound is preferably used. It is possible to use various hydroxyaromatic compounds B for the steps a) and b), however the use of the same compound B is preferred.

Monohydroxy compounds are preferred such as phenol; o-, m- or p-cresol; o-, m- or p-chlorophenol; alkyl phenols such as, for example, o-, m- or p-ethylphenol, o-, m- or p-propylphenol, o-, m- or p-tert.-butylphenol, o-, m- or p-isooctylphenol, o-, m- or p-stearylphenol; o-, m- or p-phenylphenol; o-, m- or p-cyclohexylphenol; o-, m- or p-methoxyphenol; 2,6-dimethylphenol, 2,4-dimethylphenol, 3,4-dimethylphenol; 1-naphthol or 2-naphthol, phenol is particularly preferably utilized.

In reference to the quaternary salts A that are suitable within the framework of the present invention, the quaternary cation $Q^{n+}$ may denote compounds corresponding to the formula $(XR_o^+)_t$, wherein X stands for a Group Va or VIa atom, o stands for an integer between 0 and 4, and R stands for $C_6$- to $C_{18}$-aryl, $C_7$- to $C_{18}$-aralkyl or $C_1$- to $C_{20}$-alkyl radicals, independently of one another. These include ammonium salts, guanidinium salts, phosphonium salts or sulfonium salts, optionally also mixtures thereof, substituted with organic radicals. The letter n stands for a natural number; t=n. Oligomers having t>1 may also be utilized, however monomeric ions (t=1) are preferred. Ammonium ions, guanidinium ions, phosphonium ions, sulfonium ions and sulfoxonium ions, which have as the organic radicals $C_6$- to $C_{18}$-aryl, $C_7$- to $C_{18}$-aralkyl or $C_1$- to $C_{20}$-alkyl radicals are suitable for use in the process according to the invention. The radicals may in each case all be identical or may be different and may themselves be substituted. Two substituent radicals may in each case be replaced by a ring. Mixtures of a plurality of quaternary cations may optionally also be utilized.

The following ions might be listed as examples: tetramethylammonium, tetra-n-ethylammonium, tetra-n-propylammonium, tetra-n-butylammonium, di-n-decyldimethylammonium, di-n-octadecydimethylammonium, tri-n-decyl-methylammonium, N-methyl-N-decylmorpholinium, N-methyl-N-ethylpyrrolidinium, N-(2-hydroxyethyl)-N-ethylpiperidinium, benzyltributylammonium, phenyltrimethylammonium, tetraphenylammonium, tetramethylphosphonium, tetra-n-ethylphosphonium, tetra-n-propylphosphonium, tetra-n-butylphosphonium, di-n-decyldimethylphosphonium, di-n-octadecyldimethylphosphonium, tri-n-decylmethylphosphonium, benzyltributylphosphonium, phenyltrimethylphosphonium, tetraphenylphosphonium, hexaethylguanidinium, tetramethylbishexylguanidinium.

Tetraalkylammonium ions, tetraarylammonium ions, tetraalkylphosphonium ions, tetraarylphosphonium ions and hexaalkylguanidinium ions are preferably utilized.

Tetrabutylammonium ions, tetrabutylphosphonium ions or tetraphenylphosphonium ions are particularly preferably utilized.

Halides, nitrates, sulfates, hydrogen sulfates, carbonates, hydrogen carbonates, tetrafluoroborates, carboxylates, phosphates, hydrogen phosphates or dihydrogen phosphates and hexafluorophosphates may, for example, be utilized as a counter-anion to the quaternary cations $Y^{m-}$. Here, the letter m stands for an integer between 1 and 3. Mixtures of various anions are possible. Halides such as chloride and bromide are preferred, particularly preferably bromide.

Preferred combinations are tetraalkylammonium halides and tetraphenylphosphonium halides, particularly preferably tetrabutylammonium bromide, tetrabutylammonium chloride, tetraphenylphosphonium bromide and tetrabutylphosphonium bromide. The quantity which is utilized of such a quaternary salt may be, for example, from 0.01 to 30 wt. %, in relation to the weight of the reaction mixture.

Embodiments which make use of the parameters, compounds, definitions and explanations named as being preferred, particularly preferred or most particularly preferred are preferred, particularly preferred or most particularly preferred.

The aforementioned general definitions, parameters, compounds and explanations or those mentioned in areas of preference may, however, also be combined at will with one another, that is to say between the areas and the areas of preference in each case.

The process is applicable to very widely varied reaction products C, preferably reaction products that are poorly soluble in water. Since the presence of hydroxyaromatic compounds is sometimes necessary for the process according to the invention, the process is most suitable in respect to reaction products in which phenol or other hydroxyaromatic compounds are in any case utilized as an educt, auxiliary substance, catalyst or other reaction component. The products of such reactions are therefore preferred.

Examples are etherifications, esterifications, substitution reactions, oxidations and reductions of hydroxyaromatic compounds. A particularly attractive example is the direct carbonylation of phenol, in which diphenyl carbonate is generated from carbon monoxide, oxygen and phenol. Reaction products of B are therefore preferred as the product C, particularly preferably diaryl carbonates, most particularly preferably diphenyl carbonate.

The reaction mixtures in the context of the invention are characterised by the presence of the solvent or solvents, one or more quaternary salts A, one or more hydroxyaromatic compounds B and one or more reaction products C.

As has been mentioned, such reaction mixtures occur in the oxidative direct carbonylation of hydroxy aromatics. Mixtures are obtained there which typically contain solvent (for example chlorobenzene), phenol (B), diphenyl carbonate (C), as well as impurities, by-products, optionally also further catalyst components such as palladium compounds, compounds of the metal co-catalyst, ligands thereof, organic co-catalysts and other auxiliary substances.

One or more further separation steps to remove valuable reaction components such as the catalyst compound, for example a Pd compound, or the co-catalyst optionally precede the process according to the invention for the separation of the quaternary salts.

In the oxidative direct carbonylation of phenol the incomplete selectivity of the reaction is problematic. For example, oxidative C or O coupling reactions of the hydroxyaromatics B may take place alongside the carbonylation. For their part, the resulting reaction products have hydroxyaromatic groups and are optionally more highly reactive than phenol as regards further coupling and carbonylation reactions. If these impurities are not removed they lead to an ever-decreasing reaction selectivity. They may furthermore condense to oligomeric compounds which may bring about an undesirable increase in the viscosity of the reaction medium. Oligomeric impurities must therefore in particular be removed.

It has surprisingly been established that these objects may be achieved by variations on the extraction method according to the invention.

The invention therefore also provides a process II for the separation of reaction by-products D resulting upon the reaction(s) of one or more of quaternary salts A, hydroxyaromatic compounds B and reaction main products C, wherein D is at least one member of the group consisting of 2-phenoxyphenol, 4-phenoxyphenol, salicylic acid phenyl ester, 2-bromophenol, 4-bromophenol, 2-cumyl phenol, 4-cumyl phenol, 2,2'-dihydroxybiphenyl, 2,4'-dihydroxybiphenyl, 4,4'-dihydroxybiphenyl, as well as di- or oligo(aryl carbonates), di- and oligo(phenoxy phenols), oligo (phenoxy phenol carbonates), biphenol monocarbonates and biphenyl dicarbonates, which are generated from these hydroxyaromatic compounds or phenol by combinations of carbonylations and oxidative couplings, and Where the total weight of D is less than the weight of C, comprising working up at least once the material system that contains the solution from process 1, which comprises DA, B and C, to obtain α in step a) an aqueous phase containing the quaternary salt A, and an organic phase which contains C and β separating C from the organic phase by crystallisation or preferably by distillation to obtain C and, D, and χ working up the aqueous phase obtained following step a) is worked up according to step b), and returning the organic phase which contains at least some D into the reaction.

As experiments have shown, the distribution coefficient of phenol is greater than one. It has furthermore been shown that most of the compounds generated by reaction between two phenol components have even greater distribution coefficients. It is well known to those skilled in the art that the hydrophilicity of an aromatic compound reduces as the number of aromatic hydroxy groups falls and as the number of non-hydroxy-functionalized aromatic groups rises. Hence each O-coupling step and carbonylation step leads to a greater distribution coefficient which at some time ensures that the impurities returned into the reaction by way of the extraction into the aqueous phase, and subsequent re-extraction into an organic phase, are actually also extracted into the organic phase during a subsequent extraction in step a). It is for this reason, therefore, that an undesirable build-up of the concentration of oligomeric by-products is prevented in a loop mode of operation.

Since it has surprisingly been established in the process according to the invention that the efficiency of the individual extraction steps is highly dependent on the mass fraction of B ($c_B$) relative to A ($c_A$) in the organic solution, low mass fractions of B, to which $0.001 \cdot c_A < (c_B) < 4 \cdot c_A$ applies are preferably used for the step a1). A mass fractions ratio of $0.01 \cdot c_A < (c_B) < 3 \cdot c_A$ is particularly preferred, most particularly preferably $0.1 \cdot c_A < (c_B) < 1.5 \cdot c_A$. Particularly low B mass fractions improve the efficiency of this reaction step, yet lead, under some circumstances, to higher cost or optionally to a greater thermal loading if separation or depletion of B, for example by distillation, is necessary before the extraction. It may furthermore be worthwhile to match the distribution coefficients of A and any disruptive impurities, by varying the phenol concentration within the range indicated, such that only a small proportion of the impurities is extracted into the water phase and their concentrations does not build up during the course of the reaction after re-extraction and recirculation.

The ratio of mass fractions $c_B$ and $c_A$ is preferably regulated by way of varying the $c_B$. The mass fraction of B ($c_B$) before the extraction may be adjusted in various ways. The reaction time and the starting mass fraction of B are here preferably controlled such that the desired $c_B$ is attained at the end by the conversion. Since this procedure may lead to comparatively low space-time yields, alternative concentration control possibilities may for this reason also be attractive. Further preferred possibilities are therefore to adjust the $c_B$ by dilution with solvent, by separation of excess B by distillation, or combinations of these methods. In the step b1) very high $c_B$ mass fractions are advantageously utilized. Mass fractions of B of from approximately 2 to 100 wt. % may therefore be used in the organic phase. The upper limit of $c_B$ is generally restricted by the desired $c_B$ in the return stream to the reaction, by the water uptake which increases with $c_B$ and the viscosity of the organic phase, as well as more marked B losses into the aqueous phase, and the lower limit is restricted by the efficiency of the extraction step and the selective separation of by-products. Values of from approximately 3 to 50 wt. % are preferred, particularly preferably from 10 to 25 wt. %.

The organic phase obtained in the step b1) may be returned again into the reaction. Before this, further operations may also be undertaken on this stream: for example, further educts, catalysts and other auxiliary substances may be added, components of the stream may be depleted or removed, or individual substances may be isolated and purified. Since the organic phase is water-saturated, drying of the organic phase frequently constitutes a preferred working-up means before recirculation into the reaction, in particular in the case of reactions in which water has a disruptive effect.

The sequence of a2) and b1) is carried out such that $c_B$ is greater in the step b1) than in the step a2), $c_B$ is preferably from approximately 1.2 to 1000 times as great in the step b1) as in a2), particularly preferably $c_B$ is from approximately 2 to 100 times as great in the step b1) as in a2).

It has furthermore surprisingly been found that the concentration of further electrolytes exerts a pronounced influence on the efficiency of the extraction. The step a2) is therefore preferably carried out with as low an electrolyte concentration as possible, that is to say at an ionic strength lower than approximately 0.5, particularly preferably less than 0.2, preferably with demineralised water. Conversely, a high salt concentration may influence the step b1) favourably. One embodiment of the process therefore embraces the introduction of additional electrolytes to the extraction liquid before the reaction step b1). Since increasing the salt concentration increases the distribution coefficient organic/aqueous phase of A both for step a2) and also for step b1), when a water phase is guided in a loop (see FIGS. 1–3) the adjusting of a specified concentration of an inert salt, for example of an alkali metal halide/alkaline earth metal halide or alkali metal sulfate, may be utilized as a parameter for the fine adjustment of the distribution coefficients and hence for the designing of the apparatus used for these steps.

The extractions a2), b1) and d1) may each be carried out in one step, in a plurality of steps or in continuous manner. Continuous extraction, for example counter-current extraction, is generally preferred.

Extraction processes may be utilized for the process according to the invention such as are described, for example, in KIRK-OTHMER, Encyclopedia of Chemical Technology, Fourth Edition, Volume 10, 1993, pp. 125–181 and Ullmann's Encyclopedia of Industrial Chemistry, Fifth Edition, Volume B3, Unit Operations 11, 1988, Chapter 6, Liquid—Liquid Extraction, pp. 6-1 to 6-61.

In order to carry out the process according to the invention, extraction apparatus comprised in the following classification groups may be employed, such as, for example, columns having no energy input, columns having pulsed liquid or pulse-type internals, columns having rotating internals, mixer-settlers as well as centrifugal extractors.

Spray columns, packed columns and sieve-plate columns, which differ in the dispersion of the phases, might be named as examples of columns having no energy input.

Pulse-type sieve-plate columns, having a piston pump, having a Misek or Wepuko pulsator, columns having oscillating sieve-plates as described by Prochazka or Karr, might be named as examples of columns having pulsed liquid or pulse-type internals. The rotating disk contactor (RDC), the asymmetric rotating disk extractor (ARD), the Oldshue-Rushton multiple-mixer column, the Kuhni extractor, the Scheibel column, the SHE extractor and the Graesser contactor might be named as examples of columns having rotating internals.

The Davy McKee mixer-settler, the Lurgi tower mixer-settler tower, the IMI, General Mills and box-type mixer-settlers as described by Denver might be named as examples of mixer-settler extractors.

The Podbielniak centrifugal extractor and the Robatel centrifugal extractor might be named as examples of centrifugal extractors.

Here, the extractors may be operated as single extractors, parallel extractors or as cascades of extractors. If cascades of extraction apparatus are employed, apparatus from one classification group or various classification groups may be operated concurrently in one cascade. In a cascade the phases may be guided in co-current or preferably in counter-current manner.

The individual extraction steps a2), b1) and d1) are preferably carried out in mixer-settler batteries consisting of approximately 1 to 5 apparatus or extraction columns, particularly preferably a2) and b1) are carried out in pulse-type packed columns.

Figure 1:
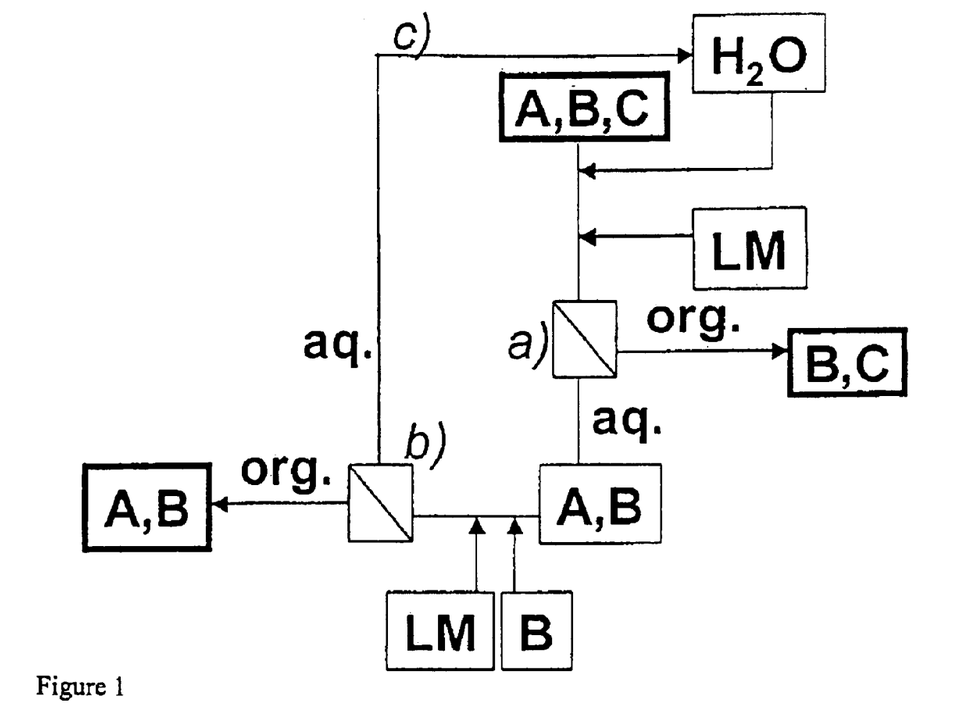
FIG. 1 is a schematic representation of an embodiment of process I according to the invention.

FIG. 1 shows an illustrative embodiment of the process according to the invention.

A reaction mixture of quaternary salts (A), hydroxy aromatic (B) and reaction product (C), which either comprises solvent (LM) and/or is diluted with LM, is extracted against an aqueous phase (step a2).

The organic phase (org.) comprises product C together with B and may be separated subsequently by known separation methods such as crystallisation and distillation, wherein B may be isolated or a B-rich stream may be generated.

The aqueous phase (aq.) comprises quaternary salt A alongside B. By the addition of solvent and additional B, for example the addition of a stream which has been obtained when working up the product, an extraction mixture is generated which enables A together with B to be converted again into an organic phase (step b1). The organic stream which is generated may be returned again into the reaction, optionally following further working-up or purification steps, for example removal of by-products, or drying.

The aqueous phase which substantially still comprises only a certain proportion of B may, for example, be used as a water phase in the first extraction. This creates a water loop, and a product stream (B, C) and a quaternary salt stream (A, B) arise as the resulting extract streams.

Figure 2:
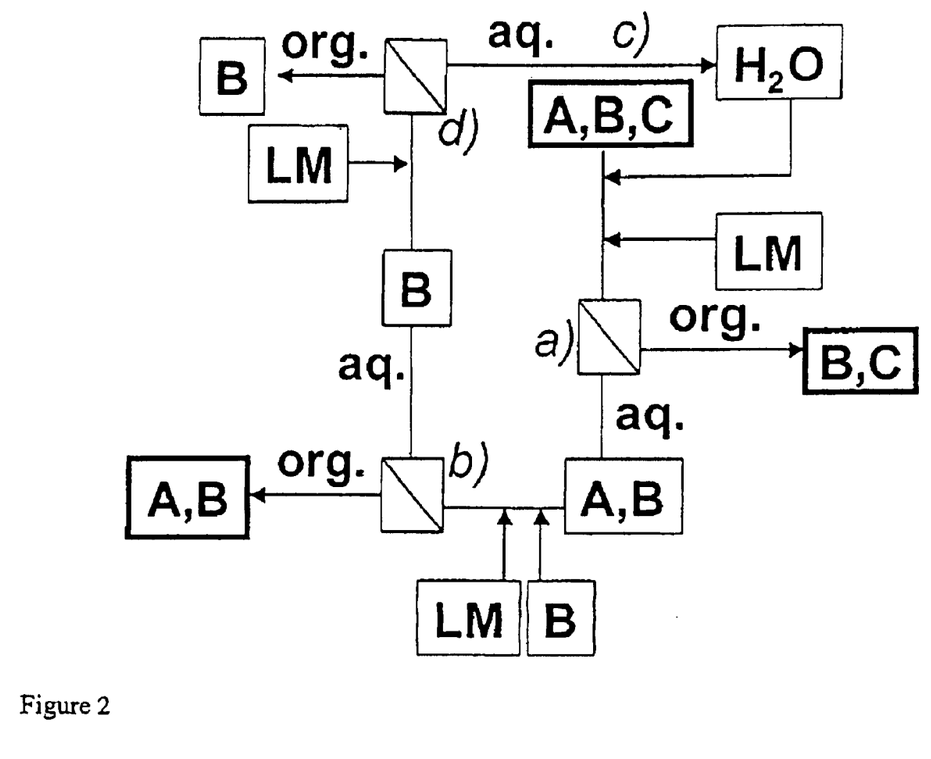
FIG. 2 shows is a schematic showing an embodiment of the process where the aqueous stream obtained from the extraction b1) is further extracted with a solvent containing low concentration of B (step d1).

Since the efficiency of the step a2) is highly dependent on the phenol concentration, it may be worthwhile reducing by means of a further working-up step the comparatively low concentration of B which is returned into the extraction mixture when the water phase is recycled. An extraction is preferred here. FIG. 2 shows an illustrative embodiment in which the aqueous stream obtained from the extraction b1) is extracted by an additional extraction with a low-B, ideally pure, solvent (step d1). Here, an organic phase of LM and B is obtained, as well as an aqueous phase which may be returned into the reaction step a2).

Figure 3:
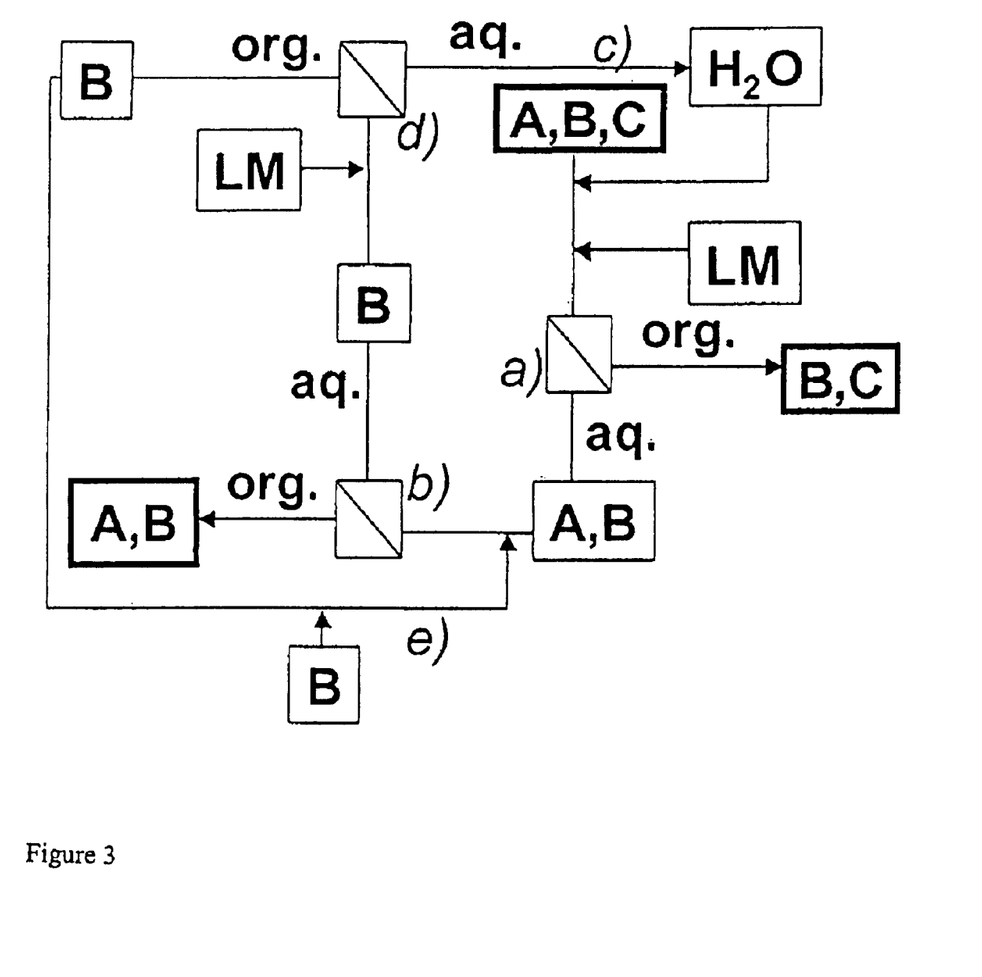
FIG. 3 is a schematic of a preferred connection scheme in which the organic phase is guided in a loop. The organic phase obtained in step d1) is utilized again in b1) as an extracting agent, after being mixed with additional quantity of B.

FIG. 3 additionally represents a preferred connection scheme in which the organic phase is likewise guided in a loop. The organic phase which is obtained in the extraction step d1) is utilized again in the step b1) as an extracting agent, after being mixed with an additional quantity of B.

Figure 4:
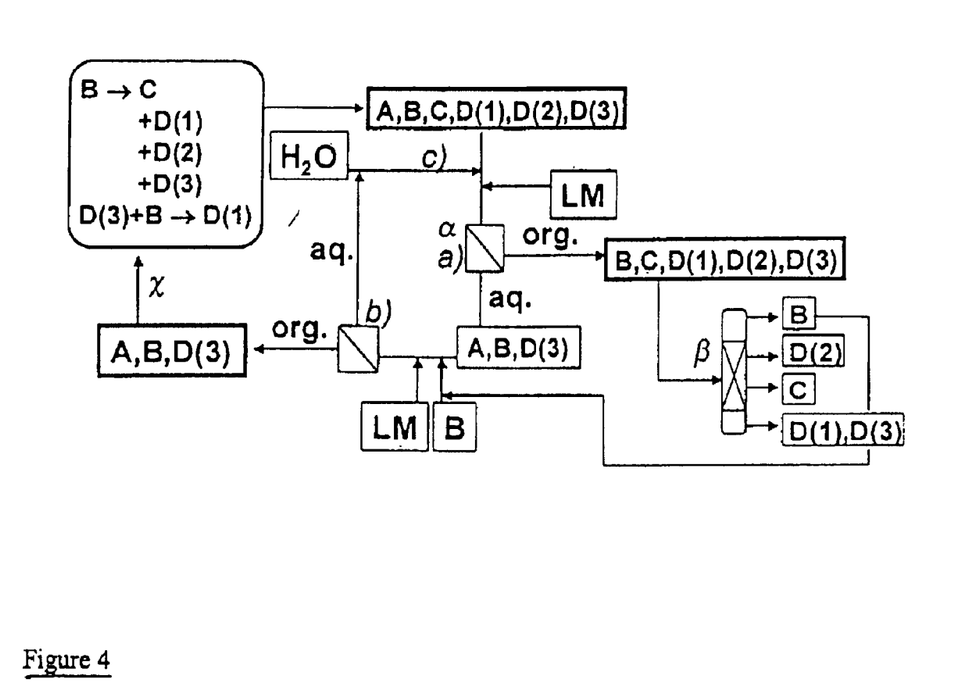
FIG. 4 is a schematic representation of an embodiment of process II for the separation of by-products.

FIG. 4 shows an illustrative embodiment of the process II for the separation of by-products. In one reaction B is converted to the desired main product C and various by-products D(1), D(2) and D(3). The reaction product D(3) still has, for example, free aromatic hydroxy groups and may react with, for example, a further B to give D(1). The reaction mixture which comprises A, B, C, D(1), D(2) and D(3) is extracted. The organic phase which comprises B, C, D(1), D(2) and possibly D(3) subsequently undergoes fractional distillation. The solvent (LM, not included in the illustration) and B are then recycled. Because of the free aromatic hydroxy groups D(3) also passes together with A and B into the aqueous phase which is again re-extracted after addition of B. After optional drying, the organic extract of A, B and D(3) is fed again into the reaction. In the reactor D(3) is converted again to D(1), as a result of which enrichment of D(3) is avoided by way of the working-up sequence.

As FIGS. 1, 2, 3 and 4 show, solvent (LM) and B at various concentrations are utilized at various points for carrying-out the processes according to the invention. Various variants of the process are conceivable to those skilled in the art, in which streams of LM and/or B arise, which may be adjusted by suitable separation, concentration and mixing operations at a desired concentration and may be connected in suitable manner within a total process, in order to generate the mixtures required for the individual extraction steps.

It is likewise known and readily determined by those skilled in the art that the process is dependent on the chemical nature of the species A, B and C and of the solvent LM, and that, depending on the distribution coefficient and the desired separation performance, the individual extractions a2), b1) or d1) must have the number of theoretical separation stages which is suitable for the specific separation problem.

EXAMPLES

Unless otherwise stated, the extractions are carried out by shaking out the phases at 80° C. for approximately half an hour. The organic phase and the aqueous phase are then examined by gas chromatography following dilution with acetone and addition of an internal standard, in order to determine the concentrations of the components. Under GC conditions tetrabutylammonium bromide (TBAB) decomposes into tributylamine and butyl bromide, which are detected. The distribution coefficient of TBAB is back-calculated from this. Distribution coefficients of the component i are generally calculated from the mass fractions $x_i$ of the components (tetrabutylammonium bromide=TBAB, monochlorobenzene=MCB, diphenyl carbonate=DPC, phenol) in accordance with $D=x_i(\text{organ. phase})/x_i$ (aqueous phase).

Example 1

33.2 g tetrabutylammonium bromide, 33.2 g diphenyl carbonate and different quantities of phenol in 195 ml chlorobenzene are extracted once with 200 ml deionised water. The results are set out in Table 1.

TABLE 1

| Phenol conc.* | 0.26 | 0.36 | 0.98 | 1.89 | 3.42 | 6.30 | 10.94 | 17.18 |
|---|---|---|---|---|---|---|---|---|
| D(TBAB) | 0.04 | 0.06 | 0.32 | 0.65 | 1.16 | 2.84 | 8.80 | 29.50 |
| D(DPC) | >1000 | >1000 | >1000 | >1000 | >1000 | >1000 | >100 | >1000 |
| D(MCB) | >500 | >500 | >500 | >500 | >500 | >500 | >500 | >500 |
| D(phenol) | 5.2 | 5.1 | 6.1 | 9.0 | 14.9 | 15.8 | n.d. | n.d. |

*as wt. % in relation to organic phase following extraction.
n.d. = not determined.

Example 2

29.0 g tetrabutylammonium bromide and 0.41 g phenol in 245 g deionised water are extracted with 250 ml chlorobenzene. Before the extraction different quantities of phenol are additionally dispensed into the chlorobenzene phase. The results are set out in Table 2.

TABLE 2

| Phenol conc.* [wt. %] | 0.08 | 0.86 | 2.50 | 4.84 | 9.49 |
|---|---|---|---|---|---|
| D(TBAB) | 0.03 | 0.27 | 1.04 | 3.18 | 13.88 |
| D(MCB) | 822 | 272 | 1269 | 225 | 88 |
| D(phenol) | 1.6 | 4.5 | 13.2 | 8.6 | 6.7 |

*in relation to organic phase following extraction.

Example 3

A solution prepared from 39.6 g tetrabutylammonium bromide, 39.6 g diphenyl carbonate, 217.8 g chlorobenzene and 3.0 g phenol is extracted a number of times with deionised water volumes which are in each case equal to the organic phase. The concentrations in the organic phase following the individual extraction steps are set out in Table 3.

TABLE 3

| Extraction step | 1 | 2 | 3 | 4 | 5 |
|---|---|---|---|---|---|
| TBAB conc. [wt. %] | 3.29 | 0.41 | 0.007 | <0.005 | <0.005 |
| DPC conc. [wt. %] | 15.1 | 15.8 | 16.2 | 16.2 | 16.2 |
| MCB conc. [wt. %] | 77.5 | 80.9 | 79.7 | 80.4 | 80.2 |
| Phenol conc. [wt. %] | 1.1 | 0.8 | 0.6 | 0.45 | 0.35 |

Example 4

A solution prepared from 29.0 g tetrabutylammonium bromide, 245.0 g water and 0.41 g phenol is extracted a number of times with volumes of 4.5 wt. % solution of phenol in chlorobenzene which are in each case equal to the aqueous phase. The concentrations in the aqueous phase following the individual extraction steps are set out in Table 4.

TABLE 4

| Extraction step | 1 | 2 | 3 | 4 |
|---|---|---|---|---|
| TBAB conc. [wt. %] | 3.22 | 0.96 | 0.38 | 0.13 |
| MCB conc. [wt. %] | 0.01 | 0.01 | 0.01 | 0.01 |
| Phenol [wt. %] | 0.40 | 0.93 | 1.40 | 1.55 |

Example 5

By means of successive additions of solid potassium bromide to a mixture of 36.0 g tetrabutylammonium bromide, 36.0 g diphenyl carbonate, 1.32 g phenol, 210 ml chlorobenzene and 250 ml water, the potassium bromide concentration in the aqueous phase is varied, and the influence on extraction is investigated. The results are set out in Table 5.

TABLE 5

| KBr concentration* | 0.1% | 1.0% | 9.8% |
|---|---|---|---|
| D(TBAB) | 0.11 | 0.15 | 1.42 |
| D(DPC) | 579 | 621 | 751 |
| D(phenol) | 3.8 | 4.9 | 54 |

*as wt. % of the aqueous phase utilized

Example 6

25.0 g tetrabutylammonium chloride and 0.41 g phenol in 249.1 g water are extracted with 250 ml chlorobenzene. Different quantities of phenol are then dispensed into the chlorobenzene phase. The results of the individual extractions are set out in Table 6.

TABLE 6

| Phenol conc.* [wt. %] | 0.06 | 2.26 | 4.62 | 9.22 |
|---|---|---|---|---|
| D(TBAC) | 0.002 | 0.38 | 1.38 | 7.83 |
| D(phenol) | 1.00 | 4.43 | 6.70 | 6.88 |

*as wt. % in relation to organic phase following extraction

Example 7

0.2 g tributylamine, 2 g phenol in 20 ml chlorobenzene are extracted with 20 ml water at 20° C. A distribution coefficient of 604 is determined.

Example 8

0.2 g tributylamine in 20 ml chlorobenzene is extracted with 20 ml water at 20° C. A distribution coefficient of 0.81 is determined.

Example 9

21.1 g diphenyl carbonate, 12 g phenol, 7.7 g tetrabutylammonium bromide in 258 g chorobenzene are extracted a number of times with volumes of water which are in each case equal to the organic phase. The extractions are carried out at 30 and at 80° C. The results for the organic phase following the individual extractions are set out in Table 7.

TABLE 7

| Temperature | Extraction step | 1 | 2 | 3 | 4 | 5 |
|---|---|---|---|---|---|---|
| 30° C. | TBAB conc. [wt. %] | 1.67 | 1.29 | 0.83 | 0.42 | 0.16 |
| | D(TBAB) | 5.5 | 2.9 | 2.1 | 0.9 | 0.44 |
| | MCB conc. [wt. %] | 87.4 | 85.6 | 86.1 | 87.5 | 87.4 |
| | Phenol conc. [wt. %] | 3.5 | 2.8 | 2.6 | 1.9 | 1.3 |
| 80° C. | TBAB conc. [wt. %] | 1.32 | 0.63 | 0.15 | 0.013 | 0.003 |
| | D(TBAB) | 1.79 | 1.15 | 0.32 | 0.08 | — |
| | MCB conc. [wt. %] | 85.2 | 86.9 | 87.4 | 88.0 | 88.1 |
| | Phenol conc. [wt. %] | 3.35 | 2.6 | 1.95 | 1.4 | 1.0 |

Example 10

A solution prepared from 0.011 g diphenyl carbonate, 3.78 g tetrabutylammonium bromide, 295.2 g water and 0.9 g phenol is extracted a number of times with volumes of a 15 wt. % solution of phenol in chlorobenzene, which are in each case equal to the aqueous phase. The concentrations in the organic phases following the individual extraction steps are set out in Table 8.

TABLE 8

| Temperature | Extraction step | 1 | 2 | 3 |
|---|---|---|---|---|
| 30° C. | TBAB conc. [wt. %] | 0.772 | 0.013 | 0.003 |
| | MCB conc. [wt. %] | 83.8 | 83.4 | 83.7 |
| | Phenol [wt. %] | 12.4 | 14.5 | 14.80 |
| 80° C. | TBAB conc. [wt. %] | 0.88 | 0.006 | 0.001 |
| | MCB conc. [wt. %] | 85.4 | 83.0 | 82.8 |
| | Phenol [wt. %] | 12.3 | 14.3 | 14.8 |

Example 11

20 g of a mixture prepared from 60 wt. % DPC, 38.6 wt. % phenol, 0.4 wt. % silicylic acid phenyl ester, 0.2 wt. % 4-bromophenol, 0.2 wt. % 2,2'-dihydroxybiphenyl, 0.2 wt. % 4,4'-dihydroxybiphenyl, 0.2 wt. % 4-phenoxyphenol and 0.2 wt. % 4-cumyl phenol are dissolved with 80 g chlorobenzene and extracted with 100 g water. The following distribution coefficients are determined:D(phenol)=1.9; D(DPC)>100; D(salicylic acid phenyl ester)>10; D(4-bromophenol)>10; D(2,2'-dihydroxybiphenyl)>10; D(4,4'-dihydroxybiphenyl)=1.2; D(4-phenoxyphenol)>10 and D(4-cumyl phenol)>10.

Example 12

A solution (OP0) from an experiment on the oxidative direct carbonylation of phenol in chlorobenzene is extracted with water in a mass ratio of approx. 2:3 (OP1: WP1) in an extraction column. The organic phase (OP1) is separated, and the water phase (WP1) is then extracted with a solution of 16 wt. % phenol in MCB in a mass ratio of approx. 1:2 (OP2: WP2). Here, an organic solution OP2 arises. MALDI-TOF-MS investigations of the solutions OP0 and OP1 show in both cases similar intensities within the mass range 370 to approximately 1000 g/mol, to which in each case oxidative coupling products of the phenol having degrees of polymerisation of approximately 3 to 10, as well as of their monocarbonates or dicarbonates and the respective lithium adducts, may be ascribed. (Bromophenyl)phenyl carbonate and 2 Ph-O-CO-O-Ph-Ph-OH isomers are detected in a GC-MS of OP0. They might not be detected in OP2.

Example 1 shows that the extraction step a2) functions particularly well at low phenol concentrations $c_B<3$ wt. %, and that the product diphenyl carbonate (C) remains in the organic phase, whereas tetrabutylammonium bromide is extracted into the aqueous phase.

Example 2 illustrates that by increasing the phenol concentration to $c_B>2.5$ wt. %, the extraction step b1) functions surprisingly well and TBAB may be back-extracted into the solvent which is used for the actual reaction.

Example 3 demonstrates that at a phenol concentration of 1 wt. %, 4 theoretical stages are sufficient to separate the TBAB following step a2), whereas DPC remains completely in the organic phase.

Example 4 makes it clear that for the extraction step b1) at a phenol concentration of 3.9 wt. %, 6 to 7 theoretical stages are sufficient for the re-extraction of the TBAB.

Example 5 demonstrates that the aqueous extraction solution for a2) should advantageously be as low in electrolytes as possible. Conversely, the addition of an electrolyte may support the re-extraction of TBAB in b1).

Example 6 shows that other quaternary compounds may also be back-extracted in similar manner.

Examples 7 and 8 show the behaviour of the compound tributylamine which arises as a result of thermal decomposition of TBAB, in the extraction step a2). Tributylamine may have a disruptive effect on the reaction and should therefore not be returned into the reaction with the TBAB. It becomes clear that, in order to reduce any extraction of the tributylamine or of other disruptive components from the organic phase (and the subsequent re-extraction into the organic return stream to the reaction), yet in order to enable A to be extracted, optionally the concentration of B in a2) should not be allowed to fall below a minimum.

Example 9 demonstrates, on the one hand, that at temperatures higher than 30° C. phenol is preferentially extracted into the aqueous phase, and, on the other hand, the distribution coefficient is, surprisingly, substantially lower than at 30° C., even allowing for this effect, in particular at higher TBAB concentrations.

Example 10 makes it clear that for the extraction step b1) at both 30° C. and also 80° C. 2 to 3 theoretical stages are sufficient for the re-extraction of the TBAB at a phenol concentration of 15 wt. %.

Examples 11 and 12 show that by-products D of the oxidative direct carbonylation generally remain in the organic phase in the step a2) and are thus not returned into the reaction with the quaternary salts A. In particular oligomeric by-products are transported out of the A loop with the organic phase. Biphenyl diols, some of which may be returned into the reaction with the quaternary salts, will react in further steps to give more strongly hydrophobic oligomers which separate out from the reaction loop in a2).

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process for the removal and recovery of a quaternary salt A corresponding to the formula $(Q^{n+})_m(Y^{m-})_n$ from a reaction mixture that also contains at least one hydroxyaromatic compounds B, one or more reaction products C and an optional solvent, comprising:

a)
   a1) adjusting the mass fractions $C_A$ of A and $C_B$ of B in the reaction mixture such that $0.001 \cdot c_A < c_B < 4 \cdot c_A$, and
   a2) extracting the reaction mixture with water or with an aqueous solution to obtain an aqueous phase that contains A and an organic phase which comprises C and optionally isolating C from the organic phase, b)
   b1) extracting an aqueous phase that contains A with an organic phase that contains 2 to 100 wt. % of B relative to the overall weight of the organic phase, and
   b2) returning the organic phase into the reaction mixture optionally after isolating the quaternary salts A from the organic phase, c)
   c1) using the aqueous phase following the extraction referred to in b1) in the extraction referred to in a2), d)
   d1) extracting the water phase resulting from the extraction referred to in b1) with an organic phase before the extraction a2) to obtain a water phase having reduced content of B and an organic phase, e)
   e1) adding B to the organic phase obtained in step d1), and using the result in step b1), wherein $Q^{n+}$ denotes a hexaalkylguanidium ion or the formula $(XR_o^+)_t$, wherein X stands for a Group Va or VIa atom, o stands for an integer between 1 and 4, t stands for an integer between 1 and 10, and R stands for $C_1$–$C_{18}$-alkyl or -cycloalkyl, $C_7$- to $C_{18}$-aralkyl, $C_6$- to $C_{18}$-aryl, independently of one another, and two substituent radicals R may in each case be replaced by a ring, $Y^{m-}$ denotes one or more members of the group consisting of halides, nitrates, sulfates, hydrogen sulfates, carbonates, hydrogen carbonates, phosphates, hydrogen phosphates, dihydrogen phosphates, tetrafluoroborates, carboxylates or hexafluorophosphates, and m stands for an integer between 1 and 3, n is a natural number, B is a compound corresponding to the formula R—(OH)$_p$, where R denotes an aromatic radical and p is an integer from 1 to 4, and where the solvent has a boiling point of 30 to 200° C.

2. A process for the separation of reaction by-products, D which are generated upon carbonylations and oxidative couplings of hydroxyaromatic compounds or phenol and quaternary salts A, and reaction product C, wherein D is at least one member selected from the group consisting of 2-phenoxyphenol, 4-phenoxyphenol, salicylic acid phenyl ester, 2-bromophenol, 4-bromophenol, 2-cumyl phenol, 4-cumyl phenol, 2,2'-dihydroxybiphenyl, 2,4'-dihydroxybiphenyl, 4,4'-dihydroxybiphenyl, as well as di- or oligo(aryl carbonates), di- and oligo(phenoxy phenols), oligo (phenoxy phenol carbonates), biphenol monocarbonates and biphenyl dicarbonates, where the total weight of D is less than the weight of a main reaction product C, comprising working up at least once the material system that contains the solution from the process of claim 1 which comprises DA, B and C, to obtain in step a) an aqueous phase containing salt A, and an organic phase which contains C and then separating C from the organic phase by crystallisation or distillation to obtain C and, D, and working up the aqueous phase obtained following step a) according to step b), and returning the organic phase which contains at least some D into the reaction.

3. The process according to claim 1 in which at least one of steps a) to e) is carried out at temperatures of 28 to 98° C.

4. The process according to claim 1 in which the reaction products C includes at least one reaction product of B.

5. The process according to claim 1 in which B includes phenol and C includes diphenyl carbonate.

6. The process according to claim 1 in which $c_B$ is greater in step b1) than in step a2).

7. The process according to claim 1 in which the solvent is at least one member selected from the group consisting of hydrocarbons, halogenated hydrocarbons, aromatic solvents, ethers, chlorobenzene, dichlorobenzenes, fluorobenzene, benzene, toluene, anisole, methylene chloride, 1,2-dichloroethane, esters, ethers such as dioxane, tetrahydrofuran, tert.-butylmethyl ether and etherified glycols.

8. The process according to claim 1 wherein the mass fraction $C_B$ of the organic phase used in step b1) is 3 wt. % $<c_B<$50 wt. %.

9. The process according to claim 1 in which the organic phase obtained as a result of step b2) is dried before recirculation into the reaction.

10. The process according to claim 1 in which the mixture at least one of a2) and b1) contains an additional electrolyte.

* * * * *

UNITED STATES PATENT AND TRADEMARK OFFICE
CERTIFICATE OF CORRECTION

PATENT NO. : 6,734,325 B2
DATED : May 11, 2004
INVENTOR(S) : Claus-Peter Reisinger et al.

It is certified that error appears in the above-identified patent and that said Letters Patent is hereby corrected as shown below:

Column 14,
Line 23, replace "Via" with -- Vla --.

Signed and Sealed this

Sixteenth Day of November, 2004

JON W. DUDAS
*Director of the United States Patent and Trademark Office*